United States Patent [19]

Beall

[11] Patent Number: 4,729,892

[45] Date of Patent: Mar. 8, 1988

[54] USE OF CROSS-LINKED HYDROGEL MATERIALS AS IMAGE CONTRAST AGENTS IN PROTON NUCLEAR MAGNETIC RESONANCE TOMOGRAPHY AND TISSUE PHANTOM KITS CONTAINING SUCH MATERIALS

[75] Inventor: Paula T. Beall, Ardsley, N.Y.

[73] Assignee: Ciba-Geigy Corporation, Ardsley, N.Y.

[21] Appl. No.: 842,337

[22] Filed: Mar. 21, 1986

[51] Int. Cl.$^4$ ............... A61K 49/00; A61B 5/05; A61B 6/00

[52] U.S. Cl. ................... 424/9; 128/653; 128/654; 424/4; 436/173; 436/806

[58] Field of Search ............. 424/4, 9; 436/173, 806; 128/653, 654

[56] References Cited

U.S. PATENT DOCUMENTS

| | | | |
|---|---|---|---|
| 2,976,576 | 4/1956 | Wichterle et al. | 18/58 |
| 3,220,960 | 11/1965 | Wichterle et al. | 260/2.5 |
| 3,488,111 | 1/1970 | Isen | 351/160 |
| 3,532,679 | 10/1970 | Steckler | 260/80.72 |
| 3,639,524 | 2/1972 | Seiderman | 260/885 |
| 3,647,736 | 3/1972 | Ewell | 260/80.72 |
| 3,700,761 | 10/1972 | O'Driscoll et al. | 264/1 |
| 3,721,657 | 3/1973 | Seidermann | 526/217 |
| 3,728,317 | 4/1973 | Blank | 260/86.1 R |
| 3,758,448 | 9/1973 | Stanberger | 260/86.1 E |
| 3,767,731 | 10/1973 | Seidermann | 260/885 |
| 3,772,235 | 11/1973 | Stamberger | 260/29.6 HN |
| 3,803,093 | 4/1974 | Neefe | 260/66 |
| 3,813,447 | 5/1974 | Tanaka et al. | 260/63 UY |
| 3,816,571 | 6/1974 | O'Driscoll et al. | 264/1 |
| 3,822,196 | 7/1974 | O'Driscoll et al. | 204/159.16 |
| 3,841,985 | 10/1974 | O'Driscoll et al. | 204/159.16 |
| 4,136,250 | 1/1979 | Mueller et al. | 528/29 |
| 4,192,827 | 3/1980 | Mueller et al. | 525/123 |
| 4,224,427 | 9/1980 | Mueller et al. | 526/93 |
| 4,347,198 | 8/1982 | Ohkada et al. | 264/2.3 |

OTHER PUBLICATIONS

Runge et al., Radiology, vol. 147, pp. 789–791 (1983).
Wehrli et al, Magnetic Resonance Imaging, vol. 2, pp. 3–16 (1984).

*Primary Examiner*—Sidney Marantz
*Assistant Examiner*—Stephen C. Wieder
*Attorney, Agent, or Firm*—Michael W. Glynn; Irving M. Fishman

[57] ABSTRACT

Cross-linked hydrogel materials in the swollen state exhibit a range of nuclear magnetic resonance spin density values, spin-lattice or longitudinal relaxation ($T_1$) values, and spin-spin or transverse relaxation ($T_2$) values embracing that of the spectrum of values associated with animal and human tissues, thereby rendering such materials useful in nuclear magnetic resonance tomography equipment contrast determinations in physiological imaging and, as to those cross-linked hydrogel materials having $T_1$ and $T_2$ values substantially shorter than the surrounding tissue, such materials are useful as image contrast agents, for example, in the gastro-intestinal tract.

10 Claims, No Drawings

USE OF CROSS-LINKED HYDROGEL MATERIALS AS IMAGE CONTRAST AGENTS IN PROTON NUCLEAR MAGNETIC RESONANCE TOMOGRAPHY AND TISSUE PHANTOM KITS CONTAINING SUCH MATERIALS

BACKGROUND OF THE INVENTION

Proton nuclear magnetic resonance (NMR) tomography has become an important tool in biomedical research and medical diagnosis. The image contrast mechanisms of NMR are different from X-ray imaging, and provide substantial contrast between certain soft tissues that are nearly identical using radiological techniques. Further, conventional radiological imaging techniques involve the use of high energy electromagnetic radiation associated with potential cancer induction, whereas the low energy radio waves associated with NMR poses no such risk. However, while some soft tissues provide substantial contrast using NMR techniques, others, particularly those involving the gastrointestinal tract, yield a relatively low level of contrast in proton NMR imaging. This has prompted the development of suitable NMR contrast agents. While numerous substances, such as vegetable oils and paramagnetic metal salt solutions, such as ferric chloride solutions and solutions of gadolinium oxide, have been used to visualize the lumen of the stomach and intestines in NMR tomography, none have the coating and filling characteristics which have made barium sulfate so useful in radiological applications. Moreover, many paramagnetic metal ion containing solutions e.g. those of $Cu^{2+}$, $Cr^{3+}$, $Fe^{3+}$ and $Mn^{2+}$, are generally toxic at concentrations which sufficiently shorten the spin relaxation times, $T_1$ and $T_2$, of the solution environment to render such solutions useful NMR contrast agents. Runge et al., Radiology, Vol. 147, pp. 789–791 (1983).

Further, since conventionally available proton NMR tomography equipment is complex in terms of operator selectable paramaters, there is a need for storage stable materials especially in the form of a collection or array, which substantially mimics the range of proton density values, spin-lattice or longitudinal relaxation ($T_1$) values, and spin-spin or traverse relaxation ($T_2$) values, associated with various animal tissue, for tuning such selectable parameters. Appropriate tuning of the operator selectable parameters enables the operator to optimize the desired contrast characteristics associated with NMR tomographic images, including, for example, inversion recovering images, partial saturation images, density images, spin echo images, and the like. See in general, Wehrli et al., *Magnetic Resonance Imaging*, Vol. 2, pp. 3–16 (1984).

It has now been surprisingly discovered that synthetic substantially non-degradable cross-linked water-swellable hydrogel materials, having in the swollen state between about 5 to about 95% water and containing functional groups which interact with water, possess nuclear magnetic resonance spin density values, and $T_1$ and $T_2$ values sufficiently analogous to the spectrum of values associated with mammalian tissue, such that the aqueous swollen materials are highly useful in proton NMR tomographic imaging techniques, and overcome many of the disadvantages associated with known materials and techniques.

It has been further unexpectedly discovered that those hydrogels having $T_1$ and $T_2$ values substantially shorter than that of gastro-intestinal viscera are highly useful as proton NMR image contrast agents.

Thus, it is an object of the instant invention to provide a method of contrasting a proton NMR tomograph of the gastro-instestinal tract, or a portion thereof, by administering to a mammal, including man, an effective image contrasting amount of a physiologically tolerable, synthetic substantially non-degradable cross-linked hydrogel having, in the aqueous swollen state, spin-lattice or spin-spin relaxation values substantially shorter than the surrounding gastro-intestinal tissue environment.

It is a further object of the instant invention to provide an aqueous coating suspension or slurry of particulate swollen synthetic substantially non-degradable cross-linked hydrogel, said hydrogel having spin-lattice or spin-spin relaxation values substantially shorter than the respective spin-lattice or spin-spin average relaxation values of gastro-intestinal viscera, for use as proton NMR contrast agents.

It is yet a further object of the instant invention to provide a collection or array of storage stable swollen cross-linked hydrogel materials possessing a range of nuclear magnetic resonance spin density values, spin-lattice relaxation values and spin-spin relaxation values, embracing at least a portion of the spectrum of such values possessed by distinct anatomic mammalian tissue, and suitable for use in NMR imaging equipment for proton NMR image contrast determinations.

These and other objects of the invention are apparent from the following disclosure.

DETAILED DISCLOSURE OF THE INVENTION

One embodiment of the instant invention relates to a method of contrasting a proton NMR tomograph of the gastro-intestinal tract of a mammal, by administering to the mammal an effective image contrasting amount of a physiologically tolerable cross-linked synthetic substantially non-degradable hydrogel in particulate form, said hydrogel having, in the aqueous swollen state, spin-lattice or spin-spin relaxation times substantially shorter than the surrounding gastro-intestinal tissue environment, and subjecting the mammal to said proton NMR tomography.

The hydrogel particulate may be administered to the gastro-intestinal tract orally or rectally.

Conveniently, the hydrogel is administered as an aqueous suspension or slurry of particulate swollen cross-linked hydrogel. The size of the hydrogel particles can vary over a wide range, depending upon the desired resolution of the image desired, and the like. In general, the hydrogel particulate can range, in average diameter between about 100 and about 100 mm, preferably between about 1 mm and about 10 mm, and most preferably between about 2 mm and about 10 mm. The particulate hydrogel material may be in the form of beads, powders or granulates. Because of the cross-linked nature of hydrogels, they are substantially insoluble, but water-swellable, in aqueous media. Thus, the hydrogels are not absorbed through the gastro-intestinal walls upon administration. Accordingly, the image contrasting cross-linked hydrogels are generally well tolerated and avoid the toxic aspects associated with many paramagnetic metal ion solutions, due to the substantially non-degradable, i.e. non-digestible, nature of the hydrogel material.

In order for the aqueous swollen particulate cross-linked hydrogel material to exert an effective contrasting effect in proton NMR tomography of the gastro-intestinal tract, the hydrogen material chosen should, in the fully swollen state, exhibit relaxation time constants, $T_1$ and $T_2$, substantially less than that of gastro-intestinal viscera. In general, suitable hydrogels exhibit, at a proton resonance frequency of about 10 megahertz (MHZ), a $T_1$ relaxation time of between about 10 to about 200 milliseconds (msec), preferably between about 10 to about 150 msec, and most preferably between about 20 to about 120 msec, and a $T_2$ relaxation time of between about 1 to about 60 msec, preferably between about 1 to about 50 msec, most preferably between about 2 and about 50 msec. At about 10 megahertz, the $T_1$ value of gastro-intestinal viscera characteristically is between about 150–700, and the $T_2$ value is between about 20–100, msec.

As the proton resonance frequency is decreased, the respective $T_1$ and $T_2$ values of suitable image contrasting hydrogel materials likewise decrease, as do the $T_1$ and $T_2$ average values of gastro-intestinal viscera.

Similarly, as the proton resonance frequency of the NMR is increased, $T_1$ and $T_2$ values of suitable image contrasting hydrogel materials likewise increase, as do the average $T_1$ and $T_2$ values for the gastro-intestinal tract. The instant image contrasting materials are generally suitable throughout the conventional range of chosen proton resonance frequencies characteristically used in NMR tomography, e.g. between about 2 to about 30 MHZ.

Eligible cross-linked hydrogel materials suitable for use as contrast agents in NMR tomography of the gstro-intestinal tract are easily determined by simple comparison of sample swollen cross-linked hydrogel $T_1$ and $T_2$ values with the corresponding average value of gastro-intestinal tissue at a chosen proton resonance frequency. Such tests can be conducted in vitro, using representative actual or phantom tissue samples, or in vivo, using live test animals.

Typical hydrogels found to be suitable as NMR gastro-intestinal contrast agents characteristically contain between about 5% to about 80% water, more preferably between about 10% to about 75% water. The hydrogel is advantageously swollen with a saline solution for in vitro comparative purposes in order to mimic the environment of the gastro-intestinal tract.

Moreover, suitable synthetic substantially non-degradable hydrogel materials contain as part of the cross-linked, three dimensional matrix, hydrophilic functional groups which interact with water. As is well known, these functional groups are to a large extent responsible for the hydrophilic aqueous swelling ability of the hydrogels. Representative hydrophilic groups include hydroxyl, keto, amino, amido, ether, carboxy, sulfoxy, sulfonyl, and the like.

In general, the $T_1$ and $T_2$ relaxation times for a given hydrogel material will be proportional to the aqueous swelling ability of the material. Since the aqueous swellability can be decreased by increasing the amount of crosslinking of the hydrogel, the $T_1$ and $T_2$ values of the fully swollen hydrogel can be decreased by increasing the amount of crosslinking agent incorporated into the hydrogel material. It is believed that the $T_1$ and $T_2$ values are decreased as cross-linking is increased because the average compartment size for the absorbed water is reduced, thereby increasing the interaction between the water molecules and the hydrophilic components of the hydrogel matrix. Further, increasing the number of hydrophilic groups present in the hydrogel likewise tends to decrease the $T_1$ and $T_2$ relaxation times as the degree of interaction of absorbed water is dependent upon the amount and nature of such hydrophilic groups.

Suitable synthetic substantially non-degradable hydrogel materials include the known classes of pharmaceutically acceptable crosslinked hydrogel materials employed in the fields of soft contact lenses and pharmaceutical medicament diffusion carriers, including without limitation, those crosslinked hydrogel materials described in Wichterle et al. U.S. Pat. Nos. 2,976,576 and 3,220,960; Mueller et al. 4,136,250, 4,192,827 and 4,224,427; Siederman 3,639,524, 3,721,657 and 3,767,731; Ewell 3,647,736; O'Driscoll et al. 3,700,761, 3,822,196, 3,816,571 and 3,841,985; Steckler 3,532,679; Stamberger 3,758,448 and 3,772,235; Neefe 3,803,093; Tanaka et al. 3,813,447; Blank 3,728,317, Isen 3,488,111; and Ohkada et al. 4,347,198, the disclosures of which incorporated by reference herein, in toto.

Such hydrogels are generally prepared by polymerizing a monomer or mixture of monomers, either in the presence of a cross-linking agent to crosslink the polymer, or in the absence of a cross-linking agent to form a pre-crosslinked intermediate which is subsequently crosslinked with a crosslinking agent. Also in the polymerization step there may be present, in addition to a monomer or mixture of monomers, a polymer or prepolymer substrate upon which the monomers may be grafted, by polymerization, for example. Where mixtures of monomers are employed, the resulting copolymer may be random, alternating, block or graft copolymers depending upon the polymerization techniques, sequence of monomer addition, reaction conditions, nature and reactivity of the monomers employed, and the like.

Generally the monomer employed is hydrophilic in nature. However, mixtures of hydrophilic and hydrophobic monomers, preferably containing less than 50 mole percent hydrophobic constituents, may be employed. Alternatively, a hydrophobic monomer may be polymerized and subsequently converted to a hydrophilic species, for example as is well known in the polymerization and subsequent hydrolysis of vinyl acetate to form polyvinyl alcohol, which may then be cross-linked with glyoxal, diglycidyl ether or the like.

Suitable hydrophilic monomers commonly employed in the preparation of crosslinked hydrogels useful in the instant invention include, without limitation, acrylic and/or methacrylic acid and the water-soluble derivatives thereof such as the epoxy or hydroxy substituted lower alkyl esters thereof including e.g. the 2-hydroxyethyl, glycidyl, 3-hydroxypropyl, or 2,3-dihydroxypropyl esters thereof; the ethoxylated and polyethoxylated hydroxy substituted lower alkyl esters thereof; the di-(lower alkyl) aminoloweralkyl acrylates or methacrylates, such as the 2-(dimethylamino)ethyl acrylate, or the 2-(diethylamino)ethyl methacrylate; the water soluble amides thereof, such as the unsubstituted amides and amides substituted by one or two hydroxyloweralkyl groups, such as N-(2-hydroxyethyl)-methacrylamide; water soluble heterocyclic nitrogen containing monomers, such as N-vinylpyrolidone, N-vinyl-succinimide, N-vinyl-pyrrole, 2- and 4-vinylpyridine, 4-vinylquinoline, 4-acrylylmorpholine and the like, mono-olefinic sulfonic acids and their pharmaceutically acceptable salts, such as sodium ethylene sulfonate, sodium styrene sulfonate and the like; hydroxyloweralkyl maleates, fumarates and vinyl ethers, such as 2-hydroxyethyl monomaleate, di(2-hydroxyethyl) maleate, 2-hydroxyethyl vinyl ether, 4-hydroxybutyl vinyl ether and the like.

Preferably, for patient administration the crosslinked hydrogels are substantially free of strongly ionic groups, such as sulfonates, free amine groups and the like, which may adversely interact with gastro-intestinal fluids and upset the electrolytic balance.

Suitable hydrophobic monomers which may be employed include, without limitation, $C_{1-18}$ alkyl acrylates or methacrylates; vinyl acetate; $C_{1-18}$ alkenes which are unsubstituted or substituted by halo; acrylonitrile; styrene; di-lower alkyl-acrylamides and -methacrylamides, vinyl $C_{l-5}$ alkyl ethers, such as propyl vinyl ether, and the like.

Suitable crosslinking agents include, without limitation, divinyl benzene, ethylene glycol dimethacrylate, polyethyleneglycol dimethacrylate, glyoxal, diglycidyl ether, and macromer cross-linking agents such as polytetramethylene oxide having a molecular weight of about 1500 which is capped at both ends by isophorone diisocyanate or 2,4-toluene diisocyanate and subsequently terminated by 2-hydroxyethylmethacrylate, e.g. as described in U.S. Pat. No. 4,277,582, or a polysiloxane having a molecular weight of about 400 to about 8500 capped at both ends with 2,4-toluene diisocyanate or isophorone diisocyanate and subsequently terminated by 2-hydroxymethacrylate, e.g. as described in U.S. Pat. No. 4,136,250.

If desired, the hydrogel materials may be formulated in the presence of a radio-opaque substance, such as particulate barium sulfate, iobenzamic acid, iocarmic acid, iocetamic acid, iodamide, iodipamide and pharmaceutically acceptable salts thereof. Alternately, the hydrogels may be prepared in the presence of tomographic inhancing aids such as ferric ($Fe^{+3}$) and/or manganese ($Mn^{+5}$) salts to increase the contrast of the hydrogel material in comparison with the surrounding tissues. A preferred method of preparing hydrogel beads by suspension polymerization is described in U.S. Pat. No. 4,224,427. In such process one may incorporate the aforementioned adjuvant ingredients, e.g. for rendering such beads radio-opaque or for enhancing NMR contrast, simply by adding the adjuvant to the suspension polymerization medium. The amount of adjuvant present will vary, dependent upon the nature thereof. Preferably, no more than 10 percent by weight of hydrogel consists of such adjuvant.

The hydrogel material generally is administered to the patient orally or rectally as an aqueous slurry or suspension. As the hydrogel material is soft, flexible and substantially inert, the slurry or suspension is generally very well tolerated by the patient.

Also, a collection or array of diverse hydrogel samples, possessing varying $T_1$ and $T_2$ constants, preferably exhibiting $T_1$ and $T_2$ constants embracing at least a substantial portion of the spectrum of such constants exhibited by diverse mamalian tissues may be employed as tissue phantom kits for adjusting tomography equipment. Generally, at least three such samples are employed in such kits.

The following examples are presented for the purpose of illustration only and are not to be construed to limit the nature or scope of the invention in any manner whatsoever. All parts are by weight unless otherwise specified.

EXAMPLE 1

In accordance with the procedure set forth in Example 1 of U.S. Pat. No. 4,224,427, 48 parts by weight of a macromer, 20 parts N-vinyl pyrrolidone and 32 parts of 2-hydroxyethyl methacrylate were polymerized using 0.2 parts of tert-butyl peroctoate as a free radical initiator. The macromer consists of poly(tetramethylene oxide) glycol having an average molecular weight of approximately 2000 endcapped with isophorone diisocyanate in an amount of two moles per mole of said glycol, and terminated with 1 mole of 2-hydroxyethyl methacrylate per mole of said diisocyanate, reacted for 72 hours at room temperature. The reaction mixture of macromer and monomers with initiator are combined in about 240 parts of an aqueous suspension of magnesium hydroxide (prepared by combining about 180 parts of a 20% by weight aqueous sodium chloride solution with about 12 parts of magnesium chloride hexahydrate with stirring at about 80° C. and adding dropwise about 60 parts of a 1-normal sodium hydroxide solution) with stirring at 150 rpm under a nitrogen blanket at 80° C., the macromer:monomer mixture allowed to polymerize for 3 hours, and the temperature raised to 100° C. for one hour, after which the reaction medium is cooled to room temperature, the magnesium hydroxide suspending agent neutralized with concentrated hydrochloric acid and the reaction mixture beads isolated by filtration and washed with water to remove any residual monomer. The resulting polymer spherical beads (diameter approx. 1 mm) have a water content of approximately 56% by weight, based upon the weight of swollen crosslinked hydrogel polymer beads. Upon subjecting the swollen crosslinked polymer beads to NMR imaging at 6.4 MHz the following T values were obtained:

$T_1 = 320 \pm 34$ ms $T_2 = 52 \pm 3$ ms.

EXAMPLE 2

Following the method of Example 1 a crosslinked hydrogel in the form of beads having a diameter of approx. 1 mm and containing 30% by weight of the macromer of Example 1 and 70% by weight 2-hydroxyethyl methacrylate are prepared. The resulting aqueous swollen beads contain approximately 25% by weight water and when subjected to NMR imaging at 6.4 MHz exhibit the following T values:

$T_1 = 1330 \pm 400$ $T_2 = 294 \pm 55$.

EXAMPLE 3

Following the method of Example 1, crosslinked hydrogel beads containing 12% by weight of the macromer of Example 1, 40% by weight n-octyl methacrylate, 27% by weight hydroxyethyl methacrylate are prepared. The resulting aqueous swollen beads contain approximately 27% by weight water and when subjected to NMR imaging at 6.4 MHz exhibit the following T values:

$T_1 = 390 \pm 120$ $T_2 = 44 \pm 16$.

EXAMPLE 4

Following the method of Example 1, crosslinked hydrogel beads containing 12% of the macromer of Example 1, 21% 2-hydroxyethylmethacrylate, 21% N-vinyl pyrrolidone, 27.5% methyl methacrylate and 27.5% α-ethylhexyl acrylate are prepared. The resulting aqueous swollen beads contain about 10% water and when subjected to NMR imaging at 6.4 MHz exhibit the following T values:

$T_1 = 1800 \pm 220$ $T_2 = 340 \pm 80$.

EXAMPLE 5

Following the method of Example 1, crosslinked hydrogel beads containing 30% of the macromer of Example 1, 20% 2-hydroxyethyl methacrylate and 50% methyl methacrylate are prepared. The resulting aqueous swollen beads contain approximately 9.9% water and when subjected to NMR imaging at 6.4 MHz exhibit the following T values:

$T_1 = 1670 \pm 400$ $T_2 = 294 \pm 92$.

EXAMPLE 6

Crosslinked hydrogel buttons having a diameter of about 20 mm and a height of about 10 mm are prepared by placing in a mold a mixture of 50 parts by weight 2-hydroxyethyl methacrylate, 50 parts by weight dimethyl acrylamide and 0.5 parts ethyleneglycol dimethacrylate in the presence of about 0.1 part benzoin methyl ether as initiator and polymerizing the reaction mixture under ambient conditions in the presence of an ultraviolet light source for about 8 hours. Upon swelling the crosslinked hydrogel with water, the equilibrated swollen material contained 79.8% water by weight, and when subjected to NMR imaging at 6.4 MHz exhibits the following T values:

$T_1 = 1470 \pm 300$ ms $T_2 = 174 \pm 30$ ms.

Alternatively, the aforementioned monomer mixture is polymerized in a mold to form substantially spherical beads of crosslinked hydrogel having an average diameter of about 2 mm, which upon equilibration with water under ambient conditions contains approximately 80% water by weight.

EXAMPLE 7

Using the methods of Example 6, buttons and spherical beads, respectively, are prepared from a monomer mixture containing 75 parts 2-hydroxyethyl methacrylate, 25 parts dimethylacrylamide, 0.5 parts ethyleneglycol dimethacrylate as crosslinker and about 0.1 part benzoin methyl ether as polymerization initiator. The products, upon equilibration with water, contain approximately 59 weight percent water and having the following T values at 6.4 MHz:

$T_1 = 250 \pm 60$ $T_2 = 56 \pm 10$.

EXAMPLE 8

Using the methods of Example 6, buttons and spherical beads, respectively, are prepared from a mixture of 100 parts 2-hydroxyethyl methacrylate, 0.5 parts ethyleneglycol dimethacrylate and about 0.1 parts benzoin methyl ether. The products, upon equilibration with water, contain 39.3% water, a $T_1$ value of $1850 \pm 300$ and a $T_2$ value of $224 \pm 100$ (at 6.4 MHz).

EXAMPLE 9

Using the methods of Example 6, buttons and spherical beads, respectively, are prepared from a mixture of 75 parts 2-hydroxyethyl methacrylate, 25 parts methylmethacrylate, 0.5 parts ethyleneglycol dimethacrylate and 0.1 part benzoin methyl ether. The products upon equilibration with water, possess a water content of 22.7% by weight, a $T_1$ value of about 1050 and a $T_2$ value of $248 \pm 90$ (at 6.4 MHz).

EXAMPLE 10

Using the methods of Example 6, buttons and sperical beads, respectively, are prepared from a mixture of 80 parts methylmethacrylate, 20 parts dimethylacrylamide, 0.5 parts ethyleneglycol dimethacrylate and about 0.1 part benzoin methyl ether. The products, upon equilibration with water, had a water content of 12.5% by weight and, at 6.4 MHz, a $T_1$ value of $1440 \pm 700$ and a $T_2$ value of $234 \pm 100$.

EXAMPLE 11

Using the methods of Example 6, buttons and spherical beads, respectively, are prepared from a mixture of 30 parts 2-hydroxyethyl methacrylate, 40 parts methyl methacrylate, 30 parts dimethylacrylamide, 0.5 parts ethyleneglycol dimethacrylate and about 0.1 part benzoin methyl ether. The products, upon equilibration with water, have a water content of 27.6% by weight and at 6.4 MHz exhibit a $T_1$ of $220 \pm 110$ and a $T_2$ of $40 \pm 19$.

EXAMPLE 12

Using the methods of Example 6, buttons and spherical beads, respectively, are prepared from a mixture of 70 parts methyl methacrylate, 30 parts dimethyl acrylamide, 0.5 parts ethyleneglycol dimethacrylate, and 0.1 part benzoin methyl ether. The products produced posess upon equilibration with water, a water content of 22.8% and, at 6.4 MHz, a $T_2$ value of $38 \pm 50$.

EXAMPLE 13

Upon the methods of Example 6, buttons and spherical beads, respectively, are prepared from a mixture of 50 parts of a fluorinated methacrylate ester of the formula $$R_f\text{—}CH_2CH_2\text{—}SCONHCH_2CH_2OCO\text{—}C(CH_3)=CH_2$$

wherein $R_f$ is a 1:1 mixture of $n\text{-}C_8F_{17}$ and $n\text{-}C_{10}F_{21}$, 30 parts methyl methacrylate and 20 parts dimethyl acrylamide, with 0.2 parts ethyleneglycol dimethacrylate and about 0.1 part benzoin methyl ether. The fluorinated methacrylate is prepared by combining one mole of perfluoroalkylthiol of the formula $R_fCH_2CH_2SH$ per mole of 2-isocyanatoethyl methacrylate, adding to the reaction mixture 0.005 mole triethylamine per mole of thiol with mixing under ambient conditions to promote the reaction, reacting the resulting mixture at about 30° C. for 6 hours, and washing the resulting product with ethanol to remove unreacted material.

The crosslinked hydrogel, upon equilibration in water, had a water content of 11.6%, and, at 6.4 MHz, a $T_1$ value of 730±300 and a $T_2$ value of 172±105.

EXAMPLE 14

Using the methods of Example 6, buttons and spherical beads, respectively, are prepared from a mixture of 50 parts methyl methacrylate, 50 parts hydroxyethyl methacrylate, 0.5 parts ethylene glycol dimethacrylate, and about 0.1 part benzoin methyl ether. The resulting crosslinked hyrogel upon equilibration exhibits a water content of 13.9%, a $T_1$ value of 300±200 and a $T_2$ value of about 64 at 6.4 MHz.

EXAMPLE 15

A siloxane macromer is prepared according to Example 8 of U.S. Pat. No. 4,136,250. A mixture of 30 parts of the siloxane macromer, consisting of polydimethyl siloxane triol (Dow Corning 1248) having a molecular weight of about 6000 which is endcapped with isophorone diisocyanate in an amount of 3 moles per mole of siloxane and terminated with 2-hydroxyethyl methacrylate in an amount of 3 moles per mole siloxane, is combined with 40 parts methyl methacrylate and 30 parts dimethyl acrylamide, and 0.1 parts dimethyl acrylamide, and 0.1 part azobisiso-butyronitrile catalyst. The mixture is then cast as buttons having a dimater of about 20 mm and a height of about 10 mm, and as spherical beads having an average diameter of about 2 mm and cured at a temperature of 50° for 16 hours following by a post cure of 100° C. for one hour. Upon equilibration with water, the cross-linked polymer had a water content of 27.1%, and at 64 MHz a $T_1$ value of 170±70 and $T_2$ value of 42±7.

EXAMPLE 16

The procedure of Example 15 is repeated using 30 parts of the siloxane macromer with 20 parts of dimethyl/acrylamide and 50 parts methyl methacrylate. The resulting products upon equilibration contain 13.4% water and at 6.4 MHz have a $T_1$ value of 290±50.

EXAMPLE 17

An array of aqueous swollen hydrogel buttons of Examples 6, 13, 14 and 15 are aligned in a whole body NMR imaging device at 6.4 MHz to obtain $T_1$ values of 1470±300 ms, 730±300, 300±200 and 170±70. This compares favorably with tissue samples subjected to NMR imaging at 6.4 $MH_2$, i.e. the $T_1$ value of minced brain obtained is 1470±300; pancreas tissue is 730±300; heart muscle is 390±120; and liver is 170±70.

EXAMPLE 18

Using the procedure of Example 15, the macromer of Example 1 is reacted with various amounts of selected monomers to obtain crosslinked hydrogels which after equilibration in water are subjected to NMR imaging at 5 MHz to obtain the following results;

| Product | Composition, %[1] | | | | | |
|---|---|---|---|---|---|---|
| | MAC | MMA | DMA | NVP | HEMA | EHA |
| 18a | 30 | | | | 70 | |
| 18b | 30 | 42 | 28 | | | |
| 18c | 20 | | 45 | 35 | | |
| 18d | 12 | 27.5 | 33 | | | 27.5 |

| Products | Properties | | |
|---|---|---|---|
| | $T_1$ | $T_2$ | % $H_2O$ |
| 18a | 155 | 16 | 23.0 |
| 18b | 34 | 4 | 25.4 |
| 18c | 43 | 4 | 49.0 |
| 18d | 115 | 17 | 8.0 |

[1] MAC = macromer of Example 1
MMA = methyl methacrylate
DMA = dimethyl acrylamide
NVP = N—vinyl pyrrolidone
HEMA = 2-hydroxyethyl methacrylate
EHA = 2-ethylhexyl acrylate When subjected to NMR imaging at 30 $MH_2$, the products of Examples 18a give a $T_1$ value of 555±50; 18b gave a $T_1$ value of 259±29, 18c gave a $T_1$ value of 252±10 and 18d gave a $T_1$ value of 252±8. The products of 18b and 18c are especially useful due to their high contrast, as image contrast agents. All of the products of 18a–18d are useful as image contrast agents in NMR imaging machines employing a combination of $T_1$ and $T_2$ in their imaging technique.

Also, the hydrogels of Examples 7, 11, 15 and 16 are highly valuable as image contrast agents due to their high contrast in the gastro-intestinal tract.

What is claimed is:

1. A method of contrasting a proton NMR tomograph of the gastro-intestinal tract, or a portion thereof, by administering enterally to a mammal an effective image contrasting amount of a physiologically tolerable, synthetic, substantially non-degradable cross-linked hydrogel having, in the aqueous swollen state, spin-lattice or spin-spin relaxation values substantially shorter than the surrounding gastro-intestinal tissue environment; and subjecting said mammal to said proton NMR tomography.

2. A method according to claim 1 wherein the hydrogel is administered as an aqueous suspension or slurry of particulate swollen cross-linked hydrogel having an average particle diameter between about 100μ and 100 mm.

3. A method according to claim 2, wherein the hydrogel exhibits in the fully swollen state of a proton reconance frequency of about 10 megahertz, a $T_1$ relaxation time between about 10 to about 200 milliseconds and a $T_2$ relaxation time of between about 1 to 60 milliseconds.

4. A method according to claim 2, wherein the hydrogel in the swollen state contains between about 5% and about 80% by weight water.

5. A method according to claim 4, wherein the hydrogel is substantially free of strongly ionic groups.

6. A method according to claim 2, wherein the hydrogel material is in the form of a bead having an average diameter between about 1 mm and 10 mm.

7. A proton nuclear magnetic resonance tomography tissue phantom kit comprising a collection of synthetic cross-linked storage stabile aqueous swollen hydrogels possessing varying $T_1$ and $T_2$ constants as proton nuclear magnetic resonance tomography contrast agents in addition to conventional proton nuclear magnetic resonance tomography tissue phantom kit components.

8. A kit according to claim 7 wherein the collection contains at least 3 diverse hydrogel samples.

9. A kit according to claim 8, wherein the hydrogels contain between about 5 and 95% water by weight.

10. A kit according to claim 9 which is suitable for use at resonance frequencies between about 2 and about 30 MHz.

* * * * *